United States Patent
Isowaki et al.

(10) Patent No.: US 8,101,654 B2
(45) Date of Patent: Jan. 24, 2012

(54) PERCUTANEOUSLY ABSORPTIVE OPHTHALMIC PREPARATION COMPRISING OLOPATADINE

(75) Inventors: Akiharu Isowaki, Kobe (JP); Tomoko Nakajima, Kobe (JP); Akira Ohtori, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 65 days.

(21) Appl. No.: 11/988,377

(22) PCT Filed: Jul. 7, 2006

(86) PCT No.: PCT/JP2006/314017
§ 371 (c)(1),
(2), (4) Date: Mar. 10, 2008

(87) PCT Pub. No.: WO2007/007863
PCT Pub. Date: Jan. 18, 2007

(65) Prior Publication Data
US 2009/0209632 A1    Aug. 20, 2009

Related U.S. Application Data

(60) Provisional application No. 60/697,368, filed on Jul. 8, 2005.

(51) Int. Cl.
*A01N 43/02* (2006.01)
*A01N 43/40* (2006.01)
(52) U.S. Cl. ..................... 514/450; 514/324
(58) Field of Classification Search ............. 514/450
See application file for complete search history.

(56) References Cited

U.S. PATENT DOCUMENTS

| 5,116,863 | A | | 5/1992 | Oshima et al. | |
|---|---|---|---|---|---|
| 5,641,805 | A | * | 6/1997 | Hayakawa et al. | 514/450 |
| 5,744,151 | A | * | 4/1998 | Capelli | 424/405 |
| 2006/0036220 | A1 | | 2/2006 | Kawahara et al. | |

FOREIGN PATENT DOCUMENTS

WO    03/002093    1/2003

OTHER PUBLICATIONS

Modica, A. (Allergies, Focus on Allergic Rhinitis), The Canadian Journal of Diagnosis/ Sep. 2003, and printed p. 1. Specifically, Modica teach in 3rd paragraph of sole p. 1.*
International Search Report issued Oct. 11, 2006 in the International (PCT) Application of which the present application is the U.S. National Stage.

* cited by examiner

*Primary Examiner* — Sreeni Padmanabhan
*Assistant Examiner* — Timothy E Betton
(74) *Attorney, Agent, or Firm* — Wenderoth, Lind & Ponack, L.L.P.

(57) ABSTRACT

The present invention provides a percutaneously absorptive preparation for preventing or treating allergic eye disease, which comprises olopatadine or a salt thereof as an active ingredient. In addition, the present invention provides a method for preventing or treating allergic eye disease, which comprises applying a percutaneously absorptive preparation comprising olopatadine or a salt thereof to the skin surface including the skin surface of an eyelid, thereby casing transfer of a therapeutically effective amount of olopatadine or a salt thereof from the preparation to an anterior ocular segment through the skin of the eyelid rather than a systemic blood flow. The present preparation can exert a pharmacological effect over a prolonged period by a single application, as compared to conventional preparations such as eye drops.

12 Claims, No Drawings

PERCUTANEOUSLY ABSORPTIVE OPHTHALMIC PREPARATION COMPRISING OLOPATADINE

This application is a U.S. national stage of International Application No. PCT/JP2006/314017 filed Jul. 7, 2006, and claims the benefit of U.S. provisional application Ser. No. 60/697,368 filed Jul. 8, 2005.

TECHNICAL FIELD

The present invention relates to a percutaneously absorptive preparation for preventing or treating allergic eye disease, which comprises olopatadine or a salt thereof as an active ingredient. In addition, the present invention relates to a method for percutaneously delivering a therapeutically effective amount of olopatadine or a salt thereof to an anterior ocular segment as well as a method for preventing or treating allergic eye disease. Specifically, these methods comprise applying a percutaneously absorptive preparation comprising olopatadine or a salt thereof to the skin surface including the skin surface of an eyelid, thereby causing transfer of a therapeutically effective amount of olopatadine or a salt thereof from the preparation to an anterior ocular segment.

BACKGROUND ART

U.S. Pat. No. 5,116,863 discloses olopatadine (Z-11-[3-(dimethylamino)propylidene]-6,11-dihydrodibenz [b,e]oxepin-2-acetic acid) as a compound having an anti-allergic activity.

For ophthalmic use, U.S. Pat. No. 5,641,805 discloses topical ophthalmic formulations for treating allergic eye disease which comprise olopatadine as an active ingredient. This patent describes that a preferred formulation for topical ophthalmic administration is a solution, and the solution is administered in the form of eye drops.

Conventionally, the most common dosage form of topical ophthalmic formulations is eye drops. In fact, olopatadine hydrochloride is used in the form of eye drops for treating allergic conjunctivitis. However, eye drops show low local bioavailability due to the turnover of tear fluid on the surface of the eye, and thus eye drops must be frequently administered in order to maintain a pharmacological effect on the eye. For example, commercially available eye drops comprising olopatadine hydrochloride must be administered every 6 to 8 hours (i.e. twice or more a day). In addition, many eye drops contain a preservative. As a result of the use of such eye drops over a prolonged period, the preservative could cause adverse side effects such as irritation.

In view of the above, the development of an ophthalmic preparation for treating allergic eye disease such as allergic conjunctivitis, which can persistently deliver a therapeutically effective amount of a drug to an anterior ocular segment such as conjunctiva, exert a pharmacological effect on the segment over a prolonged period, and which can decrease the risk of adverse side effects, as compared to conventional preparations such as eye drops has been desired.

One of such ophthalmic preparations is reported in WO2004/064817. WO2004/064817 discloses a percutaneously absorptive preparation which is composed of a support and a plaster layer containing a therapeutic agent for eye disease formed on the support, and applied to the skin surface including the anterior surface of an eyelid in order to transfer the therapeutic agent contained in the plaster layer to the local tissues of the eye through the skin instead of a systemic blood flow. This preparation can transfer the therapeutic agent to external eye tissues such as conjunctiva, lacrimal tissue and cornea through the skin in relatively a short time, and exert a prolonged pharmacological effect on the tissues. As a therapeutic agent for eye disease, WO2004/064817 discloses ketotifen fumarate.

However, WO2004/064817 does not disclose use of olopatadine for percutaneously absorptive preparations. In addition, U.S. Pat. No. 5,641,805 does not disclose percutaneously absorptive preparation as a dosage form of olopatadine.

DISCLOSURE OF THE INVENTION

It is therefore an object of the present invention to provide a preparation for preventing or treating an allergic eye disease, which can persistently deliver a therapeutically effective amount of olopatadine or a salt thereof to an anterior ocular segment such as conjunctiva through the skin of the eyelid rather than a systemic blood flow, exert a pharmacological effect on the segment over a prolonged period, and which can decrease the risk of adverse side effects, as compared to conventional preparations such as eye drops.

The present inventors have conducted intensive studies and found that a therapeutically effective amount of olopatadine or a salt thereof can be persistently maintained in an anterior ocular segment by controlling the content and/or skin permeability of olopatadine or a salt thereof, and/or the period of application to the skin surface including the surface of an eyelid. The present inventors have completed the present invention based on these findings. Accordingly, the present invention provides the following.

[1] A method for delivering olopatadine or a pharmaceutically acceptable salt thereof to an anterior ocular segment of a mammalian subject, which comprises applying a percutaneously absorptive preparation comprising olopatadine or a pharmaceutically acceptable salt thereof to the skin surface including the surface of an eyelid of the subject, thereby causing transfer of a therapeutically effective amount of olopatadine or a pharmaceutically acceptable salt thereof from the preparation to the anterior ocular segment of the subject.

[2] The method of [1], wherein the therapeutically effective amount of olopatadine or a pharmaceutically acceptable salt thereof is maintained in the anterior ocular segment of the subject for at least 8 hours.

[3] The method of [1], wherein the therapeutically effective amount of olopatadine or a pharmaceutically acceptable salt thereof is maintained in the anterior ocular segment of the subject for at least 16 hours.

[4] The method of [1], wherein the therapeutically effective amount of olopatadine or a pharmaceutically acceptable salt thereof is maintained in the anterior ocular segment of the subject for at least 8 hours after removal of the preparation from the skin.

[5] A method for preventing or treating an allergic eye disease in a mammalian subject, which comprises applying a percutaneously absorptive preparation comprising olopatadine or a pharmaceutically acceptable salt thereof to the skin surface including the surface of an eyelid of the subject, thereby causing transfer of a therapeutically effective amount of olopatadine or a pharmaceutically acceptable salt thereof from the preparation to an anterior ocular segment of the subject.

[6] The method of [5], wherein the therapeutically effective amount of olopatadine or a pharmaceutically acceptable salt thereof is maintained in the anterior ocular segment of the subject for at least 8 hours.

[7] The method of [5], wherein the therapeutically effective amount of olopatadine or a pharmaceutically acceptable salt thereof is maintained in the anterior ocular segment of the subject for at least 16 hours.

[8] The method of [5], wherein the therapeutically effective amount of olopatadine or a pharmaceutically acceptable salt thereof is maintained in the anterior ocular segment of the subject for at least 8 hours after removal of the preparation from the skin.

[9] The method of any of claims [1] to [8], wherein the percutaneously absorptive preparation is an adhesive preparation.

[10] The method of [9], wherein the adhesive preparation is applied to the skin surface for 0.5 to 24 hours.

[11] A percutaneously absorptive preparation comprising olopatadine or a pharmaceutically acceptable salt thereof for use in preventing or treating an allergic eye disease in a mammalian subject, which comprises applying it to the skin surface including the surface of an eyelid of the subject, thereby causing transfer of a therapeutically effective amount of olopatadine or a pharmaceutically acceptable salt thereof from the preparation to an anterior ocular segment of the subject.

[12] The preparation of [11], wherein the therapeutically effective amount of olopatadine or a pharmaceutically acceptable salt thereof is maintained in the anterior ocular segment of the subject for at least 16 hours.

[13] The preparation of [11], wherein the therapeutically effective amount of olopatadine or a pharmaceutically acceptable salt thereof is maintained in the anterior ocular segment of the subject for at least 8 hours after removal of the preparation from the skin.

[14] The preparation of any of claims [11] to [13], wherein the percutaneously absorptive preparation is an adhesive preparation.

[15] The preparation of [14], which is applied to the skin surface for 0.5 to 24 hours.

[16] A use of olopatadine or a pharmaceutically acceptable salt thereof for the production of a percutaneously absorptive preparation for preventing or treating an allergic eye disease in a mammalian subject, which comprises applying it to the skin surface including the surface of an eyelid of the subject, thereby causing transfer of a therapeutically effective amount of olopatadine or a pharmaceutically acceptable salt thereof from the preparation to an anterior ocular segment of the subject.

[17] The use of [16], wherein the therapeutically effective amount of olopatadine or a pharmaceutically acceptable salt thereof is maintained in the anterior ocular segment of the subject for at least 16 hours.

[18] The use of [16], wherein the therapeutically effective amount of olopatadine or a pharmaceutically acceptable salt thereof is maintained in the anterior ocular segment of the subject for at least 8 hours after removal of the preparation from the skin.

[19] The use of any of [16] to [18], wherein the percutaneously absorptive preparation is an adhesive preparation.

[20] The use of [19], wherein the adhesive preparation is applied to the skin surface for 0.5 to 24 hours.

BEST MODE FOR EMBODYING THE INVENTION

As used in the present specification, the term "the skin surface including the surface of an eyelid" refers to an anterior skin surface of the upper and lower eyelids and the skin surface adjacent thereto.

As used in the present specification, the term "anterior ocular segment" refers to eyelid, conjunctiva, cornea, iris, ciliary body, lacrimal tissue and the like.

Examples of the allergic eye disease include allergic conjunctivitis, vernal conjunctivitis, giant papillary conjunctivitis, atopic keratoconjunctivitis and atopic blepharitis associated with atopic dermatitis.

Olopatadine and a salt thereof can be prepared by a conventional method (for example, methods disclosed in U.S. Pat. No. 5,116,863, which is hereby incorporated by reference in the present specification).

The salt of olopatadine can be a pharmaceutically acceptable salt including, for example, inorganic acid salts such as hydrochloride, sulfate and phosphate; organic acid salts such as acetate, maleate, fumarate and tartrate; alkali metal salts such as sodium salt and potassium salt; alkaline earth metal salts such as magnesium salt and calcium salt; organic amine addition salts such as morpholine and piperidine; and amino acid addition salts such as lysine, glycine and phenylalanine. Olopatadine hydrochloride is preferably used in the present invention.

The present percutaneously absorptive preparation is in a dosage form that enables delivery of a therapeutically effective amount of olopatadine or a salt thereof by application thereof to the skin surface including the surface of an eyelid. Examples of such a dosage form include external preparations for skin such as adhesive preparation, ointment preparation, gel preparation and cream preparation, and adhesive preparation, ointment preparation and gel preparation are the preferred dosage forms for use in the present invention.

As used in the present specification, the term "adhesive preparation" refers to a preparation to be directly applied to the skin surface, such as cataplasma, patch, tape and plaster.

Any component generally used for manufacturing medicine can be added to the present percutaneously absorptive preparation, if desired. Examples of such component include base matrix for adhesive preparation, ointment base, gel base, solvent, oil, crosslinking agent, surfactant, gum, resin, pH adjuster, stabilizer, antioxidant, preservative, ultraviolet absorbent and wetting agent. In addition, in order to control skin permeability of olopatadine or a salt thereof, which is delivered to an anterior ocular segment through the skin, a percutaneous absorption enhancer can be added, if desired.

Examples of base matrix for adhesive preparation include acrylic pressure sensitive adhesive, silicone pressure sensitive adhesive and rubber pressure sensitive adhesive, and any one of them is appropriate for use. The matrix can be retained on one surface of a support generally used in a preparation to be applied to the skin surface such as tape, patch, cataplasma and plaster, or on one surface of a support composed of any material having no adverse effect on the present invention.

Examples of acrylic pressure sensitive adhesive include acrylic acid-octyl acrylate copolymer, acrylate-vinyl acetate copolymer, 2-ethylhexyl acrylate-vinyl pyrrolidone copolymer and methacrylic acid-butyl acrylate copolymer.

Examples of silicone pressure sensitive adhesive include polymethylphenylsiloxane copolymer and acrylic acid-dimethylsiloxane copolymer.

Examples of rubber pressure sensitive adhesive include styrene-isoprene-styrene copolymer, natural rubber, polyisobutylene, polybutene and ethylene-vinyl acetate copolymer (EVA), to which tackifier resin, softener and the like can be added, if desired.

Examples of ointment base include fat and oil bases such as Vaseline™, paraffin, plastibase, silicone, vegetable oil, lard, wax and unguentum simplex; and emulsion bases such as hydrophilic ointment (vanishing cream), hydrophilic Vaseline™, absorption ointment, hydrous lanolin, purified lanolin and hydrophilic plastibase (cold cream).

Examples of gel base include thickening polymers such as carboxyvinyl polymer, polyacrylic acid, sodium polyacrylate, methylcellulose, polyvinyl alcohol, polyvinyl pyrrolidone, polyethylene oxide, polyacrylamide, gelatine, acacia gum, tragacanth, guar gum, xanthan gum, agar, chitosan and carageenan; fatty acid esters such as isopropyl myristate, isopropyl palmitate and propylene glycol oleate; fatty acids such as lactic acid, lauric acid, oleic acid, linoleic acid and linolenic acid; aliphatic alcohols such as lauryl alcohol and oleyl alcohol; and hydrocarbons such as squalene and squalane.

Examples of solvent include purified water, methanol, ethanol, 1-propanol, lower alcohol, ethyl acetate, diethyl ether, tert-butylmethyl ether, pyrrolidone, acetic acid, acetonitrile, N,N-dimethylformamide, acetone, methyl ethyl ketone, methyl isobutyl ketone, tetrahydrofuran, chloroform, toluene and xylene.

Examples of oil include volatile or involatile oil, solvent and resin. Oil is generally used in an external preparation for skin and may be in a liquid, paste or solid form at room temperature. Specifically, for example, higher alcohols such as cetyl alcohol and isostearyl alcohol; fatty acids such as isostearic acid and oleic acid; polyalcohols such as glycerol, sorbitol, ethylene glycol, propylene glycol and polyethylene glycol; and esters such as myristyl myristate, hexyl laurate, decyl oleate, isopropyl myristate and glyceryl monostearate can be mentioned.

Examples of crosslinking agent include polyisocyanate, organic peroxide, organometallic salt, alkoxide and metal chelate.

Examples of polyisocyanate include m-phenylene diisocyanate, 2,6-tolylene diisocyanate, p-xylylene diisocyanate, 4,4'-diphenylmethane diisocyanate, hexamethylene diisocyanate and isophorone diisocyanate.

Examples of organic peroxide include benzoyl peroxide, succinyl peroxide, carbonate peroxide, hydrogen peroxide, dialkyl peroxide (e.g. di(tert-butyl) peroxide) and diacyl peroxide.

Examples of organometallic salt include lead salicylate, copper salicylate, nickel salicylate, zinc acetate, zinc carbonate, manganese benzoate, magnesium citrate, iron acetate, zinc stearate, ferrous lactate, ammonium lead salicylate, ammonium zinc carbonate and ammonium zinc benzoate.

Examples of alkoxide include lithium methoxide, sodium methoxide, potassium methoxide, lithium ethoxide, sodium ethoxide, potassium ethoxide, lithium tert-butoxide, sodium tert-butoxide and potassium tert-butoxide.

Examples of metal chelate include 1-hydroxyethylidene-1,1-diphosphonic acid, disodium edetate, tetrasodium edetate dehydrate and sodium or potassium salt of citric acid, polyphosphoric acid, metaphosphoric acid, gluconic acid, phosphoric acid, ascorbic acid and succinic acid.

Examples of surfactant include anionic surfactant, cationic surfactant, nonionic surfactant and amphoteric surfactant.

Examples of anionic surfactant include fatty acid salt, alkyl sulfate, polyoxyethylene alkyl sulfate, alkyl sulfo carboxylate and alkyl ether carboxylate.

Examples of cationic surfactant include amine salt and quanternary ammonium salt.

Examples of nonionic surfactant include polysorbate 80, polyoxyethylene hydrogenated castor oil, polyoxyethylene fatty acid ester, polyoxyethylene alkyl ether and polyoxyethylene sorbitan fatty acid ester.

Examples of amphoteric surfactant include alkyl betaine, dimethylalkylglycine and lecithin.

Examples of gum and resin include sodium polyacrylate, cellulose ether, calcium alginate, carboxyvinyl polymer, ethylene-acrylic acid copolymer, vinyl pyrrolidone polymer, vinyl alcohol-vinyl pyrrolidone copolymer, nitrogen-substituted acrylamide polymer, polyacrylamide, cationic polymer such as cationic guar gum, dimethylacrylic ammonium polymer, acrylic acid-methacrylic acid copolymer, polyoxyethylene-polypropylene copolymer, polyvinyl alcohol, pullulan, agar, gelatine, chitosan, polysaccharide from tamarindo seed, xanthan gum, carageenan, high-methoxyl pectin, low-methoxyl pectin, guar gum, acacia gum, microcrystalline cellulose, arabinogalactan, karaya gum, tragacanth gum, alginate, albumin, casein, curdlan, gellan gum, dextran, cellulose, polyethyleneimine, high polymerized polyethylene glycol, cationic silicone polymer, synthetic latex, acrylic silicone, trimethylsiloxysilicate and fluorinated silicone resin.

Examples of pH adjuster include ammonia water, hydrochloric acid, citric acid, sodium citrate, acetic acid, sodium acetate, ammonium acetate, succinic acid, tartaric acid, L-sodium tartrate, sodium hydrate, potassium hydrate, sodium carbonate, sodium hydrogencarbonate, lactic acid, calcium lactate, sodium lactate, sodium fumarate, sodium propionate, boric acid, ammonium borate, maleic acid, phosphoric acid, sodium hydrogenphosphate, dl-malic acid, adipic acid, triethanolamine, diisopropanolamine, meglumine, monoethanolamine, sulfuric acid and aluminum potassium sulfate.

Examples of stabilizer include sodium bisulfite, sodium sulfite, sodium pyrosulfite, sodium formaldehyde sulfoxylate, L-ascorbic acid, erythorbic acid, L-cysteine, thioglycerol, butylated hydroxyanisole (BHA), butylated hydroxytoluene (BHT), propyl gallate, ascorbyl palmitate, dl-α-tocopherol, nordihydroguaiaretic acid, 1-hydroxyethylidene-1,1-diphosphonic acid, disodium edetate, tetrasodium edetate dehydrate, sodium citrate, sodium polyphosphate, sodium metaphosphate, gluconic acid, phosphoric acid, citric acid, ascorbic acid and succinic acid.

Examples of wetting agent include glycerol, polyethylene glycol, sorbitol, maltitol, propylene-glycol, 1,3-butanediol and hydrogenated maltose syrup.

Examples of antioxidant include sodium bisulfite, sodium sulfite, sodium pyrosulfite, sodium formaldehyde sulfoxylate, L-ascorbic acid, erythorbic acid, L-cysteine, thioglycerol, butylated hydroxyanisole (BHA), butylated hydroxytoluene (BHT), propyl gallate, ascorbyl, palmitate, dl-α-tocopherol and nordihydroguaiaretic acid.

Examples of preservative include methylparaben, propylparaben, chlorobutanol, benzyl alcohol, phenylethyl alcohol, benzalkonium chloride, phenol, cresol, thimerosal, dehydroacetic acid and sorbic acid.

Examples of ultraviolet absorbent include octyl methoxycinnamate, glyceryl monooctanoate di-para-methoxy cinnamate, 2-hydroxy-4-methoxybenzophenone, para-aminobenzoic acid, para-aminobenzoic acid glycerol ester, N,N-dipropoxy-para-aminobenzoic acid ethyl ester, N,N-diethoxy-para-aminobenzoic acid ethyl ester, N,N-dimethyl-para-aminobenzoic aid ethyl ester, N,N-dimethyl-para-aminobenzoic acid butyl ester, homomethyl N-acetylanthranilate, amyl salicylate, menthyl salicylate, homomethyl salicylate, octyl salicylate, phenyl salicylate, benzyl salicylate and p-isopropyl phenyl salicylate.

Examples of percutaneous absorption enhancer include aliphatic alcohol, fatty acid and a salt thereof, fatty acid ester, polyalcohol alkyl ether, polyoxyethylene alkyl ether, glyceride, polyalcohol medium chain fatty acid ester, polyoxyethylene sorbitan fatty acid ester, alkyl lactate ester, terpenes and organic amine. In order to control the skin permeability of olopatadine or a salt thereof, these percutaneous absorption enhancers can be used alone or in combination of two or more kinds thereof.

Examples of aliphatic alcohol include ethanol, glycerol, diethylene glycol, propylene glycol, polyethylene glycol and higher aliphatic alcohols (saturated or unsaturated higher aliphatic alcohol having 12 to 22 carbon atoms such as oleyl alcohol, lauryl alcohol and stearyl alcohol).

Examples of fatty acid and a salt thereof include capric acid, myristic acid, palmitic acid, lauric acid, stearic acid, isostearic acid, oleic acid, linoleic acid and linolenic acid, and a salt thereof (for example, sodium salt, potassium salt, magnesium salt, calcium salt and aluminium salt).

Examples of fatty acid ester include an ester of a fatty acid such as myristic acid, palmitic acid, lauric acid, stearic acid, isostearic acid, oleic acid, linoleic acid, linolenic acid, propionic acid, butyric acid, isobutyric acid, valeric acid, pivalic acid, caproic acid, heptanoic acid, malonic acid, succinic acid, glutaric acid, adipic acid, pimelic acid, crotonic acid, sorbic acid, maleic acid, fumaric acid and sebacic acid with a lower aliphatic alcohol such as methanol, ethanol, propanol, isopropanol, butanol, pentanol, hexanol, heptanol and octanol. Specific examples of fatty acid ester include isopropyl myristate, isopropyl palmitate, diisopropyl adipate and diethyl sebacate.

Examples of polyalcohol alkyl ether include an ether of a polyalcohol such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, methyl glucoside, oligosaccharide and reduced oligosaccharide with alkyl alcohol. Alkyl moiety in polyalcohol alkyl ether preferably has 6 to 20 carbon atoms.

The preferred polyoxyethylene alkyl ether has an alkyl moiety having 6 to 20 carbon atoms and a polyoxyethylene chain having 1 to 9 repeat units ($-O-CH_2CH_2-$). Examples of polyoxyethylene alkyl ether include polyoxyethylene lauryl ether, polyoxyethylene cetyl ether, polyoxyethylene stearyl ether and polyoxyethylene oleyl ether.

The preferred glyceride is glycerol ester of fatty acid having 6 to 18 carbon atoms (e.g;, monoglyceride, diglyceride, triglyceride and a mixture thereof). Examples of glyceride include glyceryl monolaurate, glyceryl monomyristate, glyceryl monostearate, glyceryl monooleate, glyceryl dilaurate, glyceryl dimyristate, glyceryl distearate, glyceryl trilaurate, glyceryl trimyristate and glyceryl tristearate.

Examples of polyalcohol medium chain fatty acid ester include ethylene glycol monocaprylate, propylene glycol monocaprylate, glycerin monocaprylate, mono 2-ethylene glycol ethylhexanoate, mono 2-propylene glycol ethylhexanoate, di(2-propylene)glycol ethylhexanoate and propylene glycol dicaprylate.

Examples of polyoxyethylene sorbitan fatty acid ester include polyoxyethylene sorbitan monolaurate, polyoxyethylene sorbitan monostearate and polyoxyethylene sorbitan monooleate.

Examples of alkyl lactate ester include methyl lactate, ethyl lactate, methyl 2-methoxy propionate and ethyl 2-methoxypropionate.

Examples of terpene include l-menthol and d-limonene.

Examples of organic amine include monoethanolamine, triethanolamine, creatinine and meglumine.

Of the aforementioned percutaneous absorption enhancers, fatty acid ester and polyoxyethylene alkyl ether are preferable, and isopropyl myristate and polyoxyethylene oleyl ether are particularly preferable.

The present percutaneously absorptive preparation comprising olopatadine or a salt thereof can be prepared by a conventional method.

The adhesive preparation (for example, cataplasma, patch, tape and plaster) can be prepared by completely mixing olopatadine or a salt thereof with base matrix and/or gum and optionally the aforementioned solvent, oil, surfactant, resin, percutaneous absorption enhancer and/or wetting agent, spreading the obtained ointment over a support composed of nonwoven fabric, textile fabric, plastic film (including sheet) or multiple film thereof and laying a release liner over the support, or spreading the obtained ointment over a release liner and laying the support over the release liner, and pressure-bonding the release liner to the support. The support preferably has enough flexibility to apply to the skin surface including the surface of an eyelid. The thickness of the support can be appropriately set according to the dosage form. The preferred support has a thickness ranging from about 10 μm to 6000 μm.

The ointment preparation can be prepared by completely mixing olopatadine or a salt thereof with an ointment base and optionally the aforementioned solvent, oil, surfactant, gum, resin, percutaneous absorption enhancer and/or wetting agent.

The gel preparation can be prepared by adding solvent to gel base, neutralizing the mixture with pH adjuster, optionally mixing the aforementioned solvent, oil, surfactant, gum, resin, percutaneous absorption enhancer and/or wetting agent into the gel base, and completely mixing olopatadine or a salt thereof into the gel base.

The cream preparation can be prepared by mixing oil phase with aqueous phase comprising olopatadine or a salt thereof to give pre-emulsified mixture, emulsifying the mixture using homomixer, and subjecting the obtained emulsion to degasification, filtration and cooling. The aqueous phase can be prepared by mixing olopatadine or a salt thereof and moisture retention agent into purified water at about 70° C. Examples of moisture retention agent include propylene glycol, hyaluronic acid, sodium hyaluronate, urea, lactic acid, glycolic acid, glycerin and pyrrolidone carboxylate. The oil phase can be prepared by mixing the aforementioned surfactant, preservative and antioxidant into oil content at about 70° C. Examples of oil content include white petrolatum, stearic acid, stearyl alcohol and cetyl alcohol.

The present percutaneously absorptive preparation can contain one or more other ingredients such as the aforementioned pH adjuster, stabilizer, antioxidant, preservative, crosslinking agent and ultraviolet absorbent as long as they do not exert an adverse influence on the present invention.

In addition, the present percutaneously absorptive preparation can contain one or more therapeutic agents other than olopatadine or a salt thereof, such as steroidal and nonsteroidal anti-inflammatory agent, anti-bacterial agent, anti-viral agent, anti-biotic agent, sulfa agent, therapeutic agent for glaucoma, vasopressor, therapeutic agent for cataract, miotic agent, mydriatic agent and vitamin as long as they do not exert an adverse influence on the present invention.

While the content of olopatadine or a salt thereof in the present preparation is appropriately set to maintain a therapeutically effective amount of olopatadine or a salt thereof for preventing or treating an allergic eye disease in an anterior ocular segment, thereby causing transfer of olopatadine or a salt thereof to an anterior ocular segment through the skin, it is generally 0.1 to 40% by weight, preferably 1 to 30% by weight, more preferably 5 to 30% by weight.

While the content of percutaneous absorption enhancer in the present preparation varies depending on the kind of the agent, and is appropriately set to maintain a therapeutically effective amount of olopatadine or a salt thereof for preventing or treating an allergic eye disease in an anterior ocular segment by controlling skin permeability of olopatadine or a salt thereof, it is generally 1 to 60% by weight, preferably 5 to 50% by weight, more preferably 10 to 40% by weight.

The proportion of the percutaneous absorption enhancer to olopatadine or a salt thereof is generally 1 to 20 parts by weight of the percutaneous absorption enhancer to 1 part by weight of olopatadine or a salt thereof, preferably 1 to 10 parts by weight of the percutaneous absorption enhancer to 1 part by weight of olopatadine or a salt thereof, and more preferably 1 to 5 parts by weight of the percutaneous absorption enhancer to 1 part by weight of olopatadine or a salt thereof.

The present preparation can be applied to the skin surface including the surface of an eyelid of a mammalian subject (for example, human, rat, mouse, guinea pig, rabbit, sheep, swine, bovine, horse, cat, dog, monkey and the like).

The amount of olopatadine or a salt thereof in an anterior ocular segment of the subject varies according to the subject to be applied to, in the case of an adult human, it is generally about 0.3 ng/g tissue to about 100 μg/g tissue, preferably about 3 ng/g tissue to about 20 μg/g tissue.

Furthermore, the period of application to the skin surface is generally about 0.5 to about 24 hours, preferably about 2 to about 12 hours, more preferably about 4 to about 8 hours. In the case of the adhesive preparation, the period of application to the skin surface is generally about 0.5 to about 24 hours, preferably about 2 to about 12 hours, more preferably about 4 to about 8 hours.

The present percutaneously absorptive preparation can persistently prevent or treat allergic eye disease by application thereof the skin surface including the surface of an eyelid, thereby causing transfer of a therapeutically effective amount of olopatadine or a pharmaceutically acceptable salt thereof from the preparation to an anterior ocular segment through the skin of the eyelid rather than a systemic blood flow. In addition, the present percutaneously absorptive preparation can maintain and/or regulate the amount of olopatadine or a salt thereof in an anterior ocular segment by controlling the content and/or skin permeability of olopatadine or a salt thereof, and/or the period of application to the skin surface including the surface of an eyelid.

Therefore, the present preparation can exert a pharmacological effect over a prolonged period by a single application, as compared to conventional preparations such as eye drops. For example, as to the present percutaneously absorptive preparation such as adhesive preparation, ointment preparation, gel preparation and cream preparation, a therapeutically effective amount of olopatadine or a salt thereof for preventing or treating allergic eye disease can be maintained in an anterior ocular segment for at least 8 hours, preferably at least 16 hours, after application of the preparation to the skin surface including the surface of an eyelid. Particularly, when the present percutaneously absorptive preparation is applied to the skin surface including the surface of an eyelid for about 8 hours, a therapeutically effective amount of olopatadine or a salt thereof for preventing or treating allergic eye disease can be maintained in an anterior ocular segment for a long time (e.g., 8 hours or more) after removal of the preparation from the skin. Furthermore, even when the present percutaneously absorptive preparation is applied to the skin surface including the surface of an eyelid for a short time (e.g., 4 to 8 hours), a therapeutically effective amount of olopatadine or a salt thereof for preventing or treating allergic eye disease can be maintained in an anterior ocular segment for a long time (e.g., 8 to 12 hours or more) after removal of the preparation from the skin.

When the adhesive preparation of the present invention is applied to the skin surface including the surface of an eyelid for about 8 hours, a therapeutically effective amount of olopatadine or a salt thereof for preventing or treating allergic eye disease can be maintained in an anterior ocular segment for a long time (e.g., 8 hours or more) after removal of the preparation from the skin.

The dose and the administration period of the present percutaneously absorptive preparation vary depending on the target disease, symptom, administration subject, administration route and the like. For example, an adhesive preparation containing olopatadine or a salt thereof in a proportion of about 0.1 to 40% by weight is adhered 1 to 5 times a day for 0.5 to 24 hr, preferably 1 to 3 times a day for 2 to 12 hr, more preferably once a day for 4 to 8 hr.

The dose of olopatadine or a salt thereof in the present percutaneously absorptive preparation is generally 0.05 mg to 5 g/day, preferably 0.1 mg to 1 g/day, more preferably 1 mg to 0.2 g/day, for an adult.

The administration period of the present percutaneously absorptive preparation is desirably 1 day to about 3 months and repetitive administration during such period is desirable.

The present invention will be described in more detail with reference to the following examples, which are not intended to limit the present invention.

EXAMPLES

Test example 1

Pharmacological Test Using a Guinea Pig Model for Histamine-Induced Chemosis of Conjunctiva 1. Preparation of Test Preparations Example 1

Adhesive Preparation Containing Olopatadine

| | |
|---|---|
| olopatadine hydrochloride | 0.3 g |
| isopropyl myristate | 1.2 g |
| acrylic-pressure sensitive adhesive (PE-300) | 1.485 g (as solids content) |
| crosslinking agent (CK401) | 0.0015 g (as solids content) |
| ethyl acetate | proper quantity |
| total amount | 3 g |

1500 tablets (about 203 g) of Allelock™ Tablets 5 (including 5 mg of olopatadine hydrochloride per one tablet; KYOWA HAKKO Co., Ltd.) were pulverized with mill (Oster, mini Blender). Pulverized powder was suspended in ethanol (500 mL), and stirred for about 1 hour at room temperature. Any insoluble matter was collected by filtration, and collected insoluble matter was subjected to the same process twice. Filtrate (about 1500 ml) was concentrated to give white solid (10.85 g). The obtained white solid was suspended in 2-propanol (100 mL) and subjected to filtration. After filtration, the solid was suspended in purified water (about 1500 mL) (pH 5 to 6), and any insoluble matter was removed by filtration. Filtrate was adsorbed to DIAION HP-20 (500 mL), washed with purified water (about 1200 mL), and subjected to desalting. The adsorbate was eluted with ethanol (1500 mL), and fractions that showed a single spot (about 300 mL) were concentrated to give white solid. The obtained solid was subjected to recrystallization using 2-propanol:purified water (3:1) solution (100 mL). After recrystallization, obtained crystal was dissolved in 2-propanol:purified water (3:1) solution (50 mL). 4N hydrochloric acid/dioxane solution (3.04 mL) was added to the crystal-dissolved solution. The solution was concentrated, and the resulting residue was subjected to recrystallization using acetone:purified-water (2:1) solution (about 100 mL). The obtained crystal was air-dried at room temperature, and dried under reduced pressure for 10 hours at room temperature to give olopatadine hydrochloride (2.6 g). The chemical structure, physical properties and purity of obtained olopatadine hydrochloride were confirmed by nuclear magnetic resonance spectrum ($^1$H-NMR), measurement of melting point, measurement of moisture content, and high-performance liquid chromatography (HPLC).

The obtained olopatadine hydrochloride was mixed with about 2 mL of ethyl acetate. The mixture was subjected to ultrasonication in disposable cup for about 30 seconds in order to dissolve or disperse olopatadine hydrochloride, and fully mixed with isopropyl myristate. Acrylic pressure sensitive adhesive 3.7125 g (PE-300; acrylate copolymer; solid content of 40% by weight (ethyl acetate/toluene mixed solvent): 1.485 g; Nippon Carbide Industries Co., Ltd.) and crosslinking agent 0.015 g (CK401; metal chelate; solid content of about 10% by weight (toluene solvent): 0.0015 g; Nippon Carbide Industries Co., Ltd.) were sequentially added to the mixture. The mixture was fully mixed and degassed. The mixture was spread over release liner using metering knife or baker applicator, and stood until the organic solvent was completely evaporated. Subsequently, support was laid over the release liner and compressed using roller, and subjected to crosslinking in temperature controlled bath for 8 to 12 hours at about 40° C. to give adhesive preparation comprising olopatadine hydrochloride.

Example 2

Ointment Preparation

| | |
|---|---|
| olopatadine hydrochloride | 0.3 g |
| isopropyl myristate | 1.2 g |
| White petrolatum | 1.5 g |
| total amount | 3 g |

Example 3

Gel Preparation

| | |
|---|---|
| olopatadine hydrochloride | 0.3 g |
| isopropyl myristate | 1.2 g |
| 2% carboxyvinyl polymer gel | 1.5 g |
| total amount | 3 g |

Example 4

Cream Preparation

| | |
|---|---|
| olopatadine hydrochloride | 1.0 g |
| stearic acid | 0.2 g |
| cetyl alcohol | 0.3 g |
| white petrolatum | 1.0 g |
| isopropyl myristate | 4.0 g |
| propylene glycol | 0.5 g |
| polysorbate 80 | 0.5 g |
| methylparaben | 0.02 g |
| propylparaben | 0.002 g |
| ascorbic acid | 0.1 g |
| potassium hydrate | proper quantity |
| purified water | proper quantity |
| total amount | 10 g |

Comparative Example 1

Eye Drops Containing Olopatadine

Commercially available 0.1% olopatadine hydrochloride-containing eye drops (Patanol™ eye drops; Alcon) were used for Comparative example 1.
2. Test Method
2-1. Animal
4-week-old male Slc:Hartley guinea pigs were purchased from Japan SLC. Each of the guinea pigs was kept in a breeding room within the conventional area-under the condition of temperature of 23±2° C. and humidity of 55±10%.
2-2. Test Groups
Table 1 shows the constitution of the test groups.

TABLE 1

| Group | the number of animals(n) |
|---|---|
| Administered with eye drops containing saline (Control) | 7 |
| Administered with eye drops of Comparative example 1 | 7 |
| Applied with adhesive preparation of Example 1 (Treatment A) | 8 |
| Applied with adhesive preparation of Example 1 (Treatment B) | 7 |

2-3. Preparation of Histamine Solution
In order to prepare 2% histamine solution, histamine dihydrochloride (Wako Pure Chemical Industries, Ltd.) was dissolved in physiological saline, and any impurity was removed through a filter having pore size of 0.22 μm (MILLEX™-GV).
2-4. Preparation of Dye (Evans Blue) Solution
In order to prepare 2% dye solution, Evans blue (Merck) was dissolved in physiological saline, and any impurity was removed through a filter having pore size of 0.22 μm (MILLEX™-GV).
2-5. Induction of Chemosis of Conjunctiva with Histamine
In order to anesthetize the test guinea pig, 0.5 mL/kg of equivalent mixture of 50 mg/mL of ketamine-containing injection solution (Ketalar™ 50 for animal; SANKYO) and 20 mg/mL xylazine injection solution (Selactar™ 2% injection solution; Bayer) was intramuscularly administered to the guinea pig in the muscle of the thigh of the hindlimb using 1 ml syringe with a 25 G needle. At 3 to 4 minutes after intramuscular administration, 1.0 mL/kg (20 mg/kg) of 2% Evans blue solution was intravenously injected to an ear of the anesthetized guinea pig using 1 mL syringe with a 30 G needle. At 5 minutes after intramuscular administration, 50 µL of aqueous histamine solution (0.2%) was injected to the conjunctiva covering the lower eyelid of the left eye and then that of the right eye using 100 µL syringe with a 30 G needle in order to induce conjunctivitis in the test guinea pig. At 30 minutes after induction of conjunctivitis, the guinea pig was sacrificed. The head of the guinea pig was shaved with electric clippers, and the eyelid and conjunctiva region, which had been stained in blue due to the enhanced vascular permeability associated with conjunctiva in the eyelid, were excised.

2-6. Administration of Test Preparations

Administration of test preparations is described as follow.

Physiological Saline:

At 0.5 hour before induction of conjunctivitis, 10 µL of eye drops containing physiological saline was administered to one eye of the guinea pig using micropipette.

Eye Drops of Comparative Example 1:

At 8 hours before induction of conjunctivitis, 10 µL of eye drops of Comparative example 1 was administered to one eye of the guinea pig using micropipette.

Adhesive Preparation of Example 1:

(Treatment A) At 8 hours before induction of conjunctivitis, 0.5 cm$^2$ (0.5 cm×1 cm) of adhesive preparation of Example 1 was applied to the skin of the left lower eyelid (shaved) of the guinea pig.

(Treatment B) At 16 hours before induction of conjunctivitis, 0.5 cm$^2$ (0.5 cm×1 cm) of adhesive preparation of Example 1 was applied to the skin of the left lower eyelid (shaved) of the guinea pig, and at 8 hours before induction of conjunctivitis, adhesive preparation of Example 1 applied was removed.

2-7. Excision of a Tissue Suffered from Chemosis of Conjunctiva and Quantitative Determination of Extracted Dye from the Excised Tissue After excision of a tissue suffered from chemosis of conjunctiva, the tissue was immersed in 0.8 mL of 1N potassium hydroxide solution, and incubated overnight at 37° C. ($CO_2$ incubator MCO-345; SANYO) in order to lyse the tissue. The obtained lysate was neutralized and dye-extracted by mixing 7.2 mL of 5:13 (V:V) mixture of 0.6N phosphoric acid and acetone into the lysate. The obtained mixture was subjected to centrifugation (3,000 rpm for 15 min). 620 nm absorption of the supernatant was measured using spectrophotometer (U-3010; Hitachi). On the other, the absorption of standard Evans blue solution was measured, and the amount of extracted dye from each sample tissues was determined from these absorptions.

2-8. Evaluation Method

The inhibitory effect on chemosis of conjunctiva was evaluated by the inhibitory rate calculated from the amount of dye extracted in each group and following formula.

inhibitory rate(%)={1−(X/N)}×100

X: average amount of extracted dye in test group
N: average amount of extracted dye in physiological saline (Control) administration group 3. Results Table 2 shows the evaluated results of pharmacological effect on guinea pig model of histamine-induced chemosis of conjunctiva.

TABLE 2

| Group | Inhibitory rate(%) | |
| --- | --- | --- |
| | Treated eye (one eye) | Untreated eye (Opposite eye) |
| Administered with eye drops of Comparative example 1 | 39.0 ± 8.8 | 31.7 ± 9.3 |
| Applied with adhesive preparation of Example 1 (Treatment A) | 64.1 ± 2.7 | 35.7 ± 4.8 |
| Applied with adhesive preparation of Example 1 (Treatment B) | 43.1 ± 6.0 | 9.3 ± 7.8 |

Each value represents mean ± standard error.

As shown in Table 2, both of the groups applied with the adhesive preparation of Example 1 (Treatments A and B) showed a higher inhibitory effect on histamine-induced chemosis of conjunctiva than did the group administered with eye drops of Comparative example 1. Particularly, the group applied with adhesive preparation of Example 1 (treatment B) showed a pharmacological effect even at 8 hours after removal of the preparation from the skin.

In addition, the eye applied with the adhesive preparation of Example 1 showed a higher inhibitory effect on histamine-induced chemosis of conjunctiva than did the opposite eye without application of the preparation.

The results show that olopatadine hydrochloride was delivered to an anterior ocular segment through the skin of the eyelid rather than a systemic blood flow.

Therefore, the present percutaneously absorptive preparation can exert a persistent pharmacological effect (anti-allergic effect) for a long time. In addition, the present preparation can locally exert a pharmacological effect by application to the skin surface including the surface of an eyelid of the eye to be treated.

Test Example 2

Evaluation of Drug Delivery to the Eye Tissue

The present percutaneously absorptive preparation is applied on the skin of upper and/or lower eyelids on the eye.

The quantity of olopatadine hydrochloride in eye tissue (tear and conjunctiva) is determined using high-performance liquid chromatography (HPLC).

INDUSTRIAL APPLICABILITY

The preparation of the present invention can persistently deliver a therapeutically effective amount of olopatadine or a salt thereof to an anterior ocular segment through the skin of the eyelid rather than a systemic blood flow, exert a pharmacological effect on the segment over a prolonged period, and can decrease the risk of adverse side effects, and therefore, can be used as an agent for preventing or treating an allergic eye disease.

This application is based on a patent application No. 60/697,368 filed in USA, the contents of which are hereby incorporated by reference in its entirety.

The invention claimed is:

1. A method for delivering olopatadine or a pharmaceutically acceptable salt thereof to an anterior ocular segment of a mammalian subject, which comprises applying a percutaneously absorptive preparation comprising 5 to 30% by weight of olopatadine or a pharmaceutically acceptable salt thereof to the skin surface including the surface of an eyelid of the subject, thereby causing transfer of a therapeutically effective amount of olopatadine or a pharmaceutically acceptable salt thereof from the preparation to the anterior ocular segment of the subject, wherein the therapeutically effective amount of olopatadine or a pharmaceutically acceptable salt thereof is maintained in the anterior ocular segment of the subject for at least 8 hours, wherein the percutaneously absorptive preparation is an adhesive preparation, and wherein a base matrix for the adhesive preparation is selected from the group consisting of an acrylic pressure sensitive adhesive, a silicone pressure sensitive adhesive and a rubber pressure sensitive adhesive.

2. The method of claim 1, wherein the therapeutically effective amount of olopatadine or a pharmaceutically acceptable salt thereof is maintained in the anterior ocular segment of the subject for at least 16 hours.

3. The method of claim 1, wherein the therapeutically effective amount of olopatadine or a pharmaceutically acceptable salt thereof is maintained in the anterior ocular segment of the subject for at least 8 hours after removal of the preparation from the skin.

4. A method for treating an allergic eye disease in a mammalian subject, which comprises applying a percutaneously absorptive preparation comprising 5 to 30% by weight of olopatadine or a pharmaceutically acceptable salt thereof to the skin surface including the surface of an eyelid of the subject, thereby causing transfer of a therapeutically effective amount of olopatadine or a pharmaceutically acceptable salt thereof from the preparation to an anterior ocular segment of the subject, wherein the therapeutically effective amount of olopatadine or a pharmaceutically acceptable salt thereof is maintained in the anterior ocular segment of the subject for at least 8 hours, wherein the percutaneously absorptive preparation is an adhesive preparation, and wherein a base matrix for the adhesive preparation is selected from the group consisting of an acrylic pressure sensitive adhesive, a silicone pressure sensitive adhesive and a rubber pressure sensitive adhesive.

5. The method of claim 4, wherein the therapeutically effective amount of olopatadine or a pharmaceutically acceptable salt thereof is maintained in the anterior ocular segment of the subject for at least 16 hours.

6. The method of claim 4, wherein the therapeutically effective amount of olopatadine or a pharmaceutically acceptable salt thereof is maintained in the anterior ocular segment of the subject for at least 8 hours after removal of the preparation from the skin.

7. The method of claim 1, wherein the adhesive preparation is applied to the skin surface for 0.5 to 24 hours.

8. A percutaneously absorptive preparation comprising 5 to 30% by weight of olopatadine or a pharmaceutically acceptable salt thereof for use in treating an allergic eye disease in a mammalian subject, which comprises applying it to the skin surface including the surface of an eyelid of the subject, thereby causing transfer of a therapeutically effective amount of olopatadine or a pharmaceutically acceptable salt thereof from the preparation to an anterior ocular segment of the subject, wherein the therapeutically effective amount of olopatadine or a pharmaceutically acceptable salt thereof is maintained in the anterior ocular segment of the subject for at least 8 hours, wherein the percutaneously absorptive preparation is an adhesive preparation, and wherein a base matrix for the adhesive preparation is selected from the group consisting of an acrylic pressure sensitive adhesive, a silicone pressure sensitive adhesive and a rubber pressure sensitive adhesive.

9. The preparation of claim 8, wherein the therapeutically effective amount of olopatadine or a pharmaceutically acceptable salt thereof is maintained in the anterior ocular segment of the subject for at least 16 hours.

10. The preparation of claim 8, wherein the therapeutically effective amount of olopatadine or a pharmaceutically acceptable salt thereof is maintained in the anterior ocular segment of the subject for at least 8 hours after removal of the preparation from the skin.

11. The preparation of claim 8, which is applied to the skin surface for 0.5 to 24 hours.

12. The method of claim 4, wherein the adhesive preparation is applied to the skin surface for 0.5 to 24 hours.

* * * * *